(12) United States Patent
Zillner

(10) Patent No.: US 8,620,931 B2
(45) Date of Patent: Dec. 31, 2013

(54) METHOD OF COMPOSING AN ONTOLOGY ALIGNMENT

(75) Inventor: Sonja Zillner, München (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/168,237

(22) Filed: Jun. 24, 2011

(65) Prior Publication Data

US 2012/0330974 A1   Dec. 27, 2012

(51) Int. Cl.
*G06F 17/30* (2006.01)

(52) U.S. Cl.
CPC ............................. *G06F 17/30017* (2013.01)
USPC .......................................................... 707/749

(58) Field of Classification Search
USPC .................. 707/748–750, 758, 766, 769–771
See application file for complete search history.

(56) References Cited

U.S. PATENT DOCUMENTS

| | | | |
|---|---|---|---|
| 7,668,910 B2 * | 2/2010 | Dinges et al. | 709/204 |
| 7,899,764 B2 * | 3/2011 | Martin et al. | 706/12 |
| 2009/0313243 A1 * | 12/2009 | Buitelaar et al. | 707/5 |
| 2010/0094874 A1 * | 4/2010 | Huber et al. | 707/740 |

OTHER PUBLICATIONS

Sonja Zillner et al., Aligning Medical Ontologies by Axiomatic Models, Corpus Linguistic Syntactic Rules and Context Information, 2011, Google, 6 pages.*
Sven Abels et al., Identification of Common Methods Used for Ontology Integration Tasks, 2005, ACM, 75-78.*
Zillner, Sonja, "Aligning Medical Ontologies by Axiomatic Models, Syntactic Rules and Context Information", Siemens AG, Munich, Germany; 6 pages.

* cited by examiner

*Primary Examiner* — Jean B Fleurantin
(74) *Attorney, Agent, or Firm* — King & Spalding L.L.P.

(57) ABSTRACT

A modular method of composing an ontology alignment provides a set of correspondences between at least two ontologies thereby allowing a composition of an optimal alignment by balancing a recall value and a precision of the alignment. A two-fold strategy is followed. By means of mapping functions a set of alignment correspondences is determined. Depending on a particular mapping function a recall value of the alignment can be improved by an extension of the set of correspondences. By filtering functions particularities of the domain are reflected and incorrect mappings are avoided. Depending on a particular filtering function a precision value of the alignment can be improved by restricting the set of correspondences.

16 Claims, 1 Drawing Sheet

TARGET ONTOLOGY

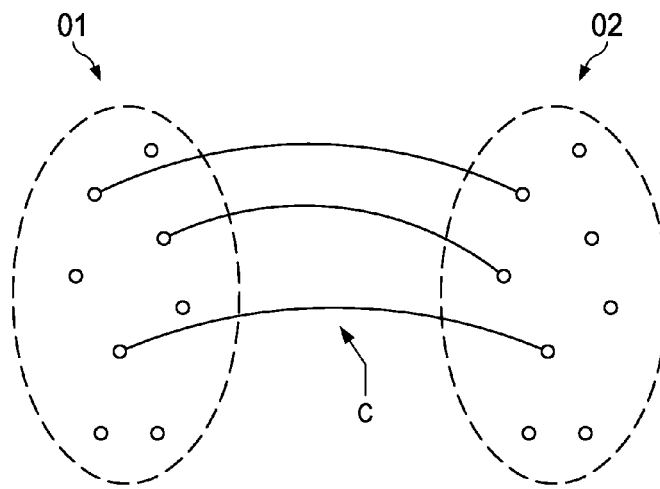
FIG. 1 TARGET ONTOLOGY
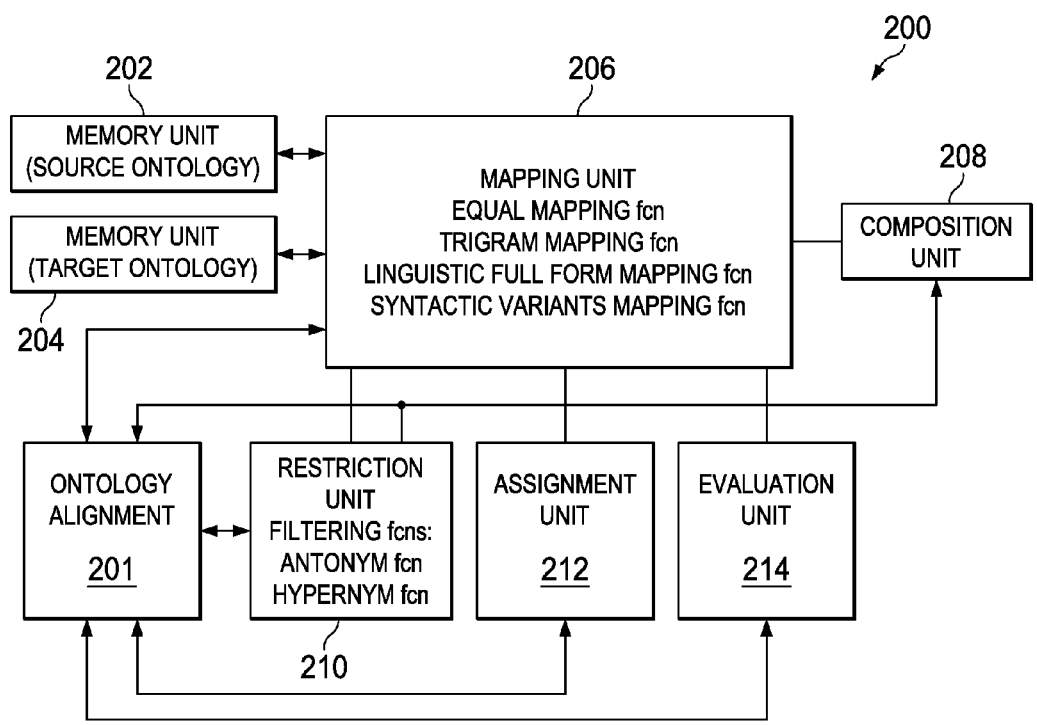
FIG. 2

METHOD OF COMPOSING AN ONTOLOGY ALIGNMENT

TECHNICAL FIELD

The invention provides a method for composing an ontology alignment for a plurality of ontologies.

BACKGROUND

An ontology is understood as a formal specification of terminology and concepts, as well as the relationships among those concepts, relevant to a particular domain or area of interest. Ontologies provide insight into the nature of information particular to a given field and are essential to any attempts to arrive at a shared understanding of the relevant concepts. They may be specified at various levels of complexity and formality depending on the domain and information needs of the participants in a given conversation.

For classical problem solving tasks, often, there is a need to use the knowledge from different multiple knowledge repositories and ontologies. This is particularly the case in the context of knowledge-rich working tasks requiring the integration of complementary knowledge from different sources and domains. One prominent example is medical imaging, where a single ontology is not enough to provide the complementary knowledge about anatomy, radiology and diseases that is required by the related applications.

Consequently, an integration of different but related types of knowledge, provisioned in disparate domain ontologies, becomes necessary.

Currently known approaches in the field of ontology alignment address this need by identifying equivalent concepts across multiple ontologies. Ontology alignment, also referred to as ontology matching or ontology mapping, is the process of determining correspondences between related or equal concepts of disparate ontologies. These concepts are then made compatible with each other through meaningful relationships.

Ontology alignment may be also understood as a special case of semantic integration that concerns a semi-automatic discovery of semantically or otherwise related concepts across two or more ontologies.

An ontology alignment may be used to align medical images with related patient text data. Any kind of application operating on these alignments is capable of delivering a coherent set of available information by contrast to solely parsing of simple keywords.

Currently known ontology alignment tools provide a development of scalable methods by combining string-based methods with complex structural methods, including tools for supporting users to tackle an interoperability problem between distributed knowledge sources. Latter tools include editors for iterative, semi-automatic mapping with incremental visualizations. However, the usage of complex methods for ontology alignment turns out to be unfeasible, particularly in the medical domain. This is mainly due to a size of a concept and relation matrix which frequently reaches a size of 100,000×100,000 alignment cells. In parallel, a creation of appropriate sub-ontologies is not possible because of complex inter-dependencies.

An alternative approach known in the art follows a pragmatic method for handling the complexity of ontologies within the medical domain. According to this approach, an information retrieval is applied in order to discover relationships between a first ontology and a second ontology by applying an indexed ontology concept to the first ontology and by matching the relationships against search queries being concepts of the second ontology. Although this approach is rather efficient and easy to implement, it does not account for the complex linguistic structure typically observed in the concept labels of medical ontologies and may also result in inaccurate matches.

SUMMARY

According to various embodiments, a method of composing an ontology alignment can be provided which is capable for ontologies up to a complex extent.

According to other embodiment, a modular method of composing an ontology alignment can be provided allowing for a flexible composition of an ontology alignment by reflecting particularities of the underlying domain, or, application scenario.

According to yet other embodiments, a modular method of composing an ontology alignment can be provided providing a set of correspondences between at least two ontologies thereby allowing for a fine-tuning of the set of correspondences.

According to yet other embodiment a modular method of composing an ontology alignment can be provided providing a set of correspondences between at least two ontologies thereby allowing a composition of an optimal alignment by balancing a recall value and a precision of the alignment.

BRIEF DESCRIPTION OF THE DRAWINGS

The invention will become more apparent and readily appreciated from the following description of various embodiments, taken in conjunction with the accompanying drawing of which:

FIG. 1 shows a source ontology aligned with a target ontology by means of correspondences.

FIG. 2 shows an exemplary block diagram of an ontology alignment system in accordance with embodiments.

DETAILED DESCRIPTION

According to various embodiments, a method for composing an ontology alignment for a plurality of ontologies, may comprise:
  providing at least one source ontology from a first memory unit, the source ontology including a plurality of structured information entities;
  providing at least one target ontology from a second memory unit, the target ontology including a plurality of structured information entities;
  processing a set of correspondences between at least one of said structured information entities of said source ontology and at least one of said structured information entities of said target ontology by applying at least one of a plurality of mapping functions;
  at least partially restricting said set of correspondences by applying at least one of a plurality of filtering functions;
  for each of said correspondences assigning an identifier for each mapping function and each filtering function being applied to provide said correspondence;
  composing a plurality of ontology alignments, each ontology alignment being a connection between an individual set of said plurality of mapping functions and an individual set of said plurality of filtering functions;
  evaluating an ontology alignment by rating a relevance of at least one of the plurality of correspondences resulting from said ontology alignment, the relevance being determined by the degree of relatedness of information entities being provided by said correspondence.

The various embodiments address deficiencies in the existing art by providing a method of composing an ontology alignment which is capable for ontologies up to a complex extent. This is achieved by aligning a source ontology to a target ontology in order to obtain an additional view to the target ontology, thereby substantially preserving the structure of both ontologies. This approach according to various embodiments allows to preserve the entire information from the target ontology for automatic image or text annotation whenever necessary.

The object of flexibility is met by enabling an adaptable composition of the ontology alignment. To this end, a two-fold strategy is followed, whereby the single steps are completed in an iterative manner:

By means of mapping functions a set of alignment correspondences is determined. Depending on a particular mapping function a recall value of the alignment can be improved by extending the set of correspondences.

By means of filtering functions particularities of the domain are reflected and incorrect mappings are avoided. Depending on a particular filtering function a precision value of the alignment can be improved by restricting the set of correspondences.

Instead of establishing the »only one¬ alignment approach, the various embodiments establish means for a flexible incorporation of domain specific constraints by defining predicates that are used by the mapping and filtering functions.

The various embodiments provide means for evaluating the composed ontology alignment by rating a relevance of the correspondences resulting from said ontology alignment.

In a possible embodiment, the quality of the ontology alignment in terms of recall and precision value can be improved by selecting alternative mapping functions and/or filtering functions, or, by adjusting connections between the mapping functions and the filtering functions.

Reference will now be made in detail to various embodiments, examples of which are illustrated in the accompanying drawing.

FIG. 1 shows a source ontology O1 including a plurality of structured information entities and a target ontology O2 including a plurality of structured information entities. The information entities are depicted by single dots without any reference sign in the drawing. Information entities of the source ontology O1 are assigned to information entities of the target ontology O2 by means of correspondences C.

The concepts of the proposed embodiment have been proofed by aligning two ontologies in the medical domain, namely the Foundational Model of Anatomy (FMA) and the Radiology Lexicon for annotating medical images (Radlex). The ontologies differ in their level of detail and coverage of particular domains. Although both ontologies have strong overlaps, both ontologies are needed for describing the required level of medical image region descriptions. This means that the alignment of these ontologies is vital for a precise semantic annotation of medical images.

FMA is the most comprehensive machine-processable resource on human anatomy. It covers 71,202 distinct anatomical concepts and about 1.5 million relation instances from 170 relation types. FMA provides synonym information, for example the synonyms Neuraxis and Central nervous system.

Radlex is a controlled vocabulary developed and maintained by the Radiological Society of North America (RSNA) for the purpose of indexing and retrieving radiology images and related information. Radlex contains more than 30000 domain related terms, e.g., anatomy pathology or imaging techniques. Synonym information is partially indicated, such as »Schatzki ring« and »Lower esophageal mucosal ring«.

For the purpose of a precise semantic annotation of medical images which aims in a semantic retrieval of image contents, a mapping between these two ontologies is required.

Ontology mapping helps to find semantically related entities of different ontologies. The mapped correspondences can then be used for required tasks over heterogeneous data resources such as semantic search, reasoning, visualization, etc.

The embodiment described hereinafter introduces a formal approach for a composite ontology alignment. The approach according to this embodiment relies on automated pre-processing of ontology alignment correspondences by syntactic rules;

the fine-tuning of alignment results by establishing context-specific axioms; and;

the continuous incorporation of user feedback for composing efficient and context-specific alignments.

Drawing upon experiences with medical ontologies, the inventor has identified some of the common characteristics of medical ontologies that are relevant for the alignment process.

These can be summarized as:

(a) medical ontologies are very large models (b) medical ontologies have extensive is-a hierarchies up to ten thousands of classes which are organized according to different views (c) medical ontologies have complex relationships in which classes are connected by a number of different relations (d) terminologies of medical ontologies are rather stable (especially for anatomy) in that they should not differ too much in the different ontologies (e) the modeling of medical ontologies principles are well defined and documented.

Furthermore, medical ontologies are typically rich in linguistic information. For example, the FMA contains concept names as long as »Anastomotic branch of right anterior inferior cerebellar artery with right superior cerebellar artery«. Such long multi-word terms are usually rich with implicit semantic relations. Ontology alignment approaches for the medical domain need to incorporate the described common characteristics of the medical ontologies.

Due to the outstanding complex nature of medical ontologies, the concepts according to various embodiments are, of course, seamlessly applicable for any kind of ontologies. The exemplary use of ontologies in the medical domain according to the described embodiment is, therefore, not restricting the proposed methods and embodiments to specific kinds of ontologies in any way.

The proposed ontology alignment framework has three main aspects. A combined strategy is suggested which is based on a) an automated linguistic-based pre-processing of ontology concepts to be aligned;

b) a fine-tuning of correspondences by formulating context-specific axioms; and;

c) a continuous evaluation of user feedback for composing effective and context-specific ontology alignments.

In the following, a formal approach is introduced and exemplified in a specific application scenario. This scenario refers to a medical image search in the context of the diagnosis and treatment of patients that suffer from lymphoma.

Lymphoma, a type of cancer affecting the lymphocytes, is a systematic disease with manifestations in multiple organs. The available image data consist of many medical images in different formats, which additionally need to be associated with the corresponding patient data.

In order to align the source ontology O1, Radlex, with the target ontology O2, FMA, the inventor had previously applied known methods based on a known basic information retrieval approach. The approach of this basic information retrieval, which is briefly described in the following, however, turned out to be unfeasible. Specifically, this approach does not account for the complex linguistic structure typically observed in the concept labels of the medical ontologies and may result in inaccurate matches.

Applying this known basic information retrieval approach, relationships between the FMA and the Radlex Taxonomy are discovered. Thereby FMA ontology concepts are treated as documents. These documents are indexed and matched against search queries, which are the concepts from the Radlex taxonomy. The »hits« related to a search are considered as similarity between the preferred name of the index term (FMA concept) and the preferred name of the search query (Radlex concept) obtained by a search engine. Every found match is treated as evidence of a correspondence.

Applying this known basic information retrieval approach could not meet the requirements which the inventor imposed for an effective and precise alignment of ontologies.

According to an embodiment, the basic information retrieval approach was replaced by an approach, which is described in the following.

An embodiment is based on incorporating mapping functions which, for example, reflect linguistic features of natural language phrases describing a particular concept. In order to cope with the complex linguistic phrase structure, mapping functions are established. These mapping functions reflect linguistic features of the natural language phrases which describe a particular concept.

The inventor's assumption is that common patterns in the multi-word terms that are typical for the concept labels in the medical ontologies can be made explicit. This means that it is assumed that »multiwords« of the ontology encompass implicit semantics. The aim is, therefore, to exploit the implicit semantics for identifying automatically ontology alignment correspondences.

Thus, the initial ontology mapping uses linguistic features of the preferred name of the ontology concepts. A subsequent evaluation by an analysis of user feedback provides guidance in fine-tuning the initial mapping results in terms of context-dependent filter functions.

As medical knowledge is a very careful and delicate context, the evaluation of ontology mapping requires the involvement of medical experts. As medical ontology are large in size, the manual mapping of medical ontologies is cumbersome and impracticable. In order to support medical experts in establishing ontology mappings, automatic pre-processing steps are required which are to be enhanced by evaluation means for continuously integrating medical expert feedback in a time-saving manner.

For enabling an efficient and transparent processing of user feedback, a need to provide explanations of the matching results arises. In other words, each established ontology mapping instance needs to incorporate the arguments of its derivation.

The key issue here is to represent explanations in a simple and clear way towards medical experts as well as knowledge engineers in order to facilitate informed decision making.

As the medical domain is complex and sensitive, an ontology alignment approach is required which allows to seamlessly merge automated and user-interactive matching and evaluation processes. The alignments need to go through an interactive evaluation loop. Eventually, the evaluation is in the assessment of properties of the obtained ontology alignment.

As to the alignment approach, modular mapping functions are introduced which are involved in the establishment of the ontology alignment according to an embodiment.

According to an embodiment, these mapping functions are subsequently enhanced by filtering functions, in order to reflect requirements of a specific application scenario. Both, mapping functions and filtering functions, finally contribute to a composition of the ontology alignment. In other words, the ontology alignment is being a connection between an individual set of a plurality of mapping functions and an individual set of a plurality of filtering functions.

In the following, some exemplary mapping functions according to alternative embodiments are introduced, thereby providing some formal definitions with regard to the terminology used herein.

Definition 1 (Ontology and Ontology Module) An ontology O is a tuple $O=(C^O, R^O)$, such that $C^O$ is the set of all concepts and $R^O$ is the set of all binary relations between the concepts. An ontology module $M=(C^M, R^M)$ of O is itself an ontology such that $C^M \subset C^O$, $R^M \subset R^O$ and $C^M \neq 0$.

Definition 2 (Ontology Alignment Correspondence) Given a source ontology $O_1=(C^{O_1}, R^{O_1})$, a target ontology $O_2=(C^{O_2}, R^{O_2})$, then an ontology alignment correspondence $\omega$ between $O_1$ and $O_2$ is a five-tuple $\omega=(id_\omega, s_\omega, t_\omega, r_\omega, \pi_\omega)$, where $id_\omega \in I$ a set of unique identifier, $s_\omega \in C^{O_1}$ denotes the source concept, $t_\omega \in C^{O_2}$ the target concept, and $r_\omega \in \{eg, \subset, \supset\}$ the type of relationship holding between $s_\omega$ and $t_\omega$, and $\pi_\omega$ denotes the mapping function, or respectively, filtering function that lead to the ontology alignment correspondence. $\Omega$ denotes the set of all ontology alignment correspondences.

Definition 3 (Mapping Function) Given a source ontology $O_1=(C^{O_1}, R^{O_1})$ and a target ontology $O_2=(C^{O_2}, R^{O_2})$, we denote $\pi$ mapping function between O1 and O2, if $\pi$ is a function, such that $\pi:C^{O_1} \times C^{O_2} \rightarrow P(\Omega)$ with $P(\omega)$ the powerset of $\Omega$.

A mapping function helps to identify a set of ontology alignment correspondences. In accordance to the requirements of the application domain, different mapping functions yield more or less valuable alignment results. An evaluation of the impact of different mapping functions and filtering functions explained below is carried out by a subsequent evaluation step.

A subsequently applied filtering function has to be considered, in a mathematical sense, as being a particular variant of a mapping function.

The final ontology alignment between two ontologies is established by a composition of different mapping functions and/or filtering functions.

Definition 4 (Ontology Alignment) Given two ontologies $O_1=(C^{O_1}, R^{O_1})$ and $O_2=(C^{O_2}, R^{O_2})$ and a set of mapping functions and/or filtering functions $\pi_1, \ldots, \pi_n$ between $O_1$ and $O_2$, then the ontology alignment $\Theta$ between $O_1$ and $O_2$ is defined as $\Theta(O_1,O_2)=\cup_{i=1}^{n} \{\pi_i(s,t) | s \in C^{O_1} \wedge t \in C^{O_2}\}$.

For establishing an ontology alignment between two ontologies, a suitable set of mapping functions is to be found that helps to extend the set of found alignment correspondences and, thus, improve the recall value of the alignment.

In the following, a composition of different mapping functions is described which serve to achieve an ontology alignment. This ontology alignment may optionally be customized for the lymphoma application scenario.

In order to reflect the requirements of a domain, the established mapping functions are further adjusted by filtering functions. These filtering functions are context-specific and establish a mechanism to improve the precision value of the alignment established by the mapping functions in a way that these filtering functions effect an elimination of incorrect mappings.

Throughout the following definitions of mapping functions, let $0_1=(C^{O_1}, R^{O_1})$ denote the source ontology, e.g. the Radlex Taxonomy, and $0_2=(C^{O_2}, R^{O_2})$ denote the target ontology, e.g. the FMA Ontology.

Four different kinds of mapping functions will be introduced in the following.

An equal mapping function $\pi_{equal}$ effects the finding of equal matches: a concept of the source ontology matches equal a concept of the target ontology if and only if each word of the preferred name of the source concepts occurs in the preferred name of the target concepts and the preferred name of source and target concept have the same length.

Definition 5 (Predicate Equal) Let $s=[s_1, \ldots, s_n]$ and $t=[t_1, \ldots, t_m]$ with n,m>0 be a multi-term expression, then the predicate $\sigma_{equal}(s,t)$ is true if and only if for all i≤n exists j≥m such that $s_i=t_j$ and n=m. Otherwise $\sigma_{equal}(s,t)$ is false.

Definition 6 (Equal Mapping Function) Let $s \in C^{O_1}$, $t \in C^{O_2}$, then the equal mapping function $\pi_{eq}:C^{O_1} \times C^{O_2} \to P(\Omega)$ is defined as $$\pi_{eq}(s,t)=\{(id,s,t,\subset,\{\pi_{eq}\})|\sigma_{equal}(s,t)\}.$$

Trigram Mapping Function

As medical concepts are long multi-term expressions, exact matches are rare. However, Radlex and FMA concepts follow a similar linguistic structure that provides guidance in identifying the most meaningful terms of the multi-term expressions. Medical concepts consist of a noun or compound noun, e.g., » lymph node «, that is often described in more detail by a list of accompanying adjectives, e.g. » right lower paratracheal «. The adjective which is adjacent to the head noun is more discriminative than the remaining adjectives.

Therefore information about nouns and adjacent adjectives needs to be considered when aligning medical concepts. This special head-modifier relationship can be detected without a complex syntactic parse tree. Instead, a trigram mapping function is provided by the following prerequisites.

Medical concepts that match equally;
a) a noun or a compound noun;
b) an adjacent adjective; and;
c) in sum at least three terms;
will be aligned.

Thus, the trigram mapping function $\pi_{trigram}$ establishes the basic pattern used for searching for ontology alignment correspondences. The trigram pattern ensures that the search string carries the relevant information.

The formal definition of the trigram mapping function relies on the predicate $\sigma_{trigram}$ which is defined as follows:

Definition 7 (Predicate Trigram) Let $s=[s_1, \ldots, s_n]$ and $t=[t_1, \ldots, t_m]$ with n,m>0 be multi-term expressions, then the predicate $\sigma_{trigram}(s,t)$ is true if and only if
for all i≤n with $s_i$ of type noun, there exists j≤m such that $s_i=t_j$; and;
for all i,j≤n with $s_i$ of type adjective and $s_j$ of type noun and i+1=j, there exists k,l≤m such that $s_i=t_k$ and $s_j=t_l$;
there exists $i_1, i_2, i_3 \leq n$ and $j_1, j_2, j_3 \leq m$ such that for all k≤3 holds $s_{i_k}=t_{j_k}$
Otherwise $\sigma_{trigram}(s,t)$ is false.

Definition 8 (Trigram Mapping Function) Let $s \in C^{O_1}$, $t \in C^{O_2}$ then the trigram mapping function $\pi_{tri}:C^{O_1} \times C^{O_2} \to P(\Omega)$ is defined as $\pi_{tri}(s,t)=\{(id,s,t,\subset,\{\pi tri\})|\sigma_{trigram}(s,t)\}$.

Generation of Linguistic Full forms

In many cases, the correspondence between two concepts cannot be found simply because the source concept is represented in singular form, e.g., » anterior cervical lymph node «, and the target concept is represented in plural form, e.g., » Anterior cervical lymph nodes «.

Even though the meaning of the concept is similar, the described mapping functions provide no means to capture the correspondence between these two concepts.

Thus, a mapping function is required which integrates the linguistic fullforms of the ontology source concept labels. The linguistic fullform mapping function $\pi_{full}$ is defined to transform multi-term expressions of the source ontology into their linguistic fullforms.

Definition 9 (Plural Form) Let M denote the set of multi-term expressions, then the plural form function $\delta_{plural}:M \to P(M)$ returns for each multi term expression its plural form.

Definition 10 (Linguistic Fullform Mapping Function) Let $s \in C^{O_1}$, $t \in C^{O_2}$, then the linguistic fullform mapping function, $\pi_{full}:C^{O_1} \times C^{O_2} \to P(\Omega)$ is defined as $$\pi_{full}(s,t)=\{(id,s,t,\subset,\{\pi_{full}\})|s' \in \delta_{plural}(s) \wedge \sigma_{trigram}(s',t)\}.$$

Syntactic Variants Function

Beside the syntactic fullform, the inventor could extend the set of correct correspondences by using information about syntactic variants of source concepts in the search for alignments. Detecting syntactic variants of ontology source concept labels helps to retrieve additional related concepts. Therefore, a syntactic variants mapping function is defined which effects a transformation of multi-word expressions of the source ontology into related syntactic variants that nevertheless preserve their semantics. One possible example of a transformation of a multi-word expression into a related syntactic variant is a noun-to-adjective conversion. Using this function, the concept labels can be transformed into semantically equivalent but syntactically different word forms.

Definition 11 (Syntactic Variants) Let M denote the set of multi-term expressions, then the syntactic variants function $\delta_{syn\_variant}:M \to P(M)$ returns for each multi-term expression its set of syntactic variants.

Definition 12 (Syntactic Variants Mapping Function) Let $s \in C^{O_1}$, $t \in C^{O_2}$, then the syntactic variants mapping function $\pi_{syn}:C^{O_1} \times C^{O_2} \to P(\Omega)$ is defined as $$\pi_{syn}(s,t)=\{(id,s,t,\subset,\{\pi_{syn}\})|s' \in \delta_{syn\_variant}(s) \wedge \sigma_{trigram}(s',t)\}.$$

In the following, a set of filtering functions according to various embodiments are provided.

Filtering functions aim to avoid incorrect mappings. An implementation of filtering functions will, therefore, lead to improved precision values. Two different filtering functions, namely an antonym filtering function and a hypernym filtering function, are presented in the following.

Antonym Filtering Function: For declaring a filtering function for antonyms adequate for the application scenario, an antonym set is defined as follows:

Definition 13 (Antonym Set) The Antonym Set $\Lambda$ is defined as $\Lambda \subset$ {(internal, external), (left, right), (deep, superficial), (internal, anterior), (external, anterior)}. The antonym relationship is symmetric, i.e. $\forall (x, y) \in \Lambda \to (y, x) \in \Lambda$.

The predicate $\sigma_{antonym}$ helps to identify ontology concepts that contain antonym terms.

Definition 14 (Predicate Antonym) Let $s=[s_1, \ldots, s_n]$ and $t=[t_1, \ldots, t_m]$ with n,m>0 be sets of multi-term expressions, then the predicate $\sigma_{antonym}$ (s,t) is true if and only if there exists i≤n and j≤m such that $(s_i, t_j) \in \Lambda$. Otherwise $\sigma_{antonym}$ (s,t) is false.

The antonym filtering function $\delta_{ant}$ helps to filter out alignment correspondences that contain antonym terms.

Definition 15 (Antonym Filtering Function) Let $W \subset \Omega$ be a set of ontology alignment correspondences, then the antonym filtering function $P(\Omega) \rightarrow P(\Omega)$ is defined as $$\delta_{ant}(W) = \{\omega \in W | \neg \sigma_{antonym}(s_\omega, t_\omega)\}.$$

In the following, the hypernym filtering function will be defined. The analysis of alignment results shows that the integration of syntactic variants helps to increase the number of correct correspondences, but, at the same time, produces a large number of incorrect alignments. In other words, recall was enhanced at the cost of precision.

By studying the feedback from clinical experts, a restriction could be defined which is based on a variant generation process: nouns should only be converted to a respective adjective form if the adjective is followed by a head noun which is a hypernym of the original head noun. Using the hypernym filtering function, defined below, a term » lymph node « can be replaced by a term » lymphatic chain « but not by a term » lymphatic vessel « .

As » lymphatic chain « consist of both, a » lymph node « and a » vessel « , there is no hypernym relationship between the two terms » node « and » vessel « . The inventor define the set of hypernym relationships that are of relevance as follows:

Definition 16 (Hypernym Set) The Hypernym Set Y is defined as $Y \subset$ {(node, chain), (node, tunk), (node, plexus), (node, tree), (vessel, chain)}. The hypernym relationship is transitive, i.e., $\forall (x, y), (y, z) \in Y \rightarrow (x, z) \in Y$.

The predicate $\sigma_{hypernym}$ allows identifying syntactic variants of ontology concepts that are correct in the application scenario.

Definition 17 (Predicate Hypernym) Let $s = [s_1, \ldots, s_n]$ and $t = [t_1, \ldots, t_m]$ with $n, m > 0$ be multi-term expressions, then the predicate $\sigma_{hypernym}$ (s,t) is true if and only if there exists i≤n and j≤m such that $(s_i, t_j) \in Y$. Otherwise $\sigma_{hypernym}$ (s,t) is false.

The hypernym filtering function helps to remove matches which could be identified by establishing syntactic variants, the syntactic variants being incorrect for the application scenario, i.e. not respecting the set hypernym relations.

Definition 18 (Hypernym Filtering Function) Let $W \in \Omega$ be a set of ontology alignment correspondences, then the hypernym filtering function $\delta_{hyp}:P(\Omega) \rightarrow P(\Omega)$ is defined as $$\delta_{hyp}(W) = \{\omega \in W | \sigma_{hypernym}(s_\omega, t_\omega)\}.$$

The inventor have evaluated and compared different ontology alignments using mapping functions described above. For a comparison, the inventor have calculated respective recall, precision, and F1-score measures. In order to obtain a reliable truth table for the test set, the inventor relied on the user rating of clinical experts, thereby relying upon inter-annotator agreements.

Using the equal mapping function $\pi_{equal}$ a Radlex concept entitled » thoracic lymph node « could be aligned with the FMA concepts » Thoracic lymph node « . A first evaluation showed that the equal mapping function produced a rather small set of alignment correspondences, i.e., 64 out of 151 Radlex concepts could be mapped onto FMA concepts.

By analyzing the Radlex concepts without hits to FMA concepts, i.e. false negatives, the inventor noticed a large number of Radlex multiterm expressions that consist of more than three terms, e.g., » right lower paratracheal lymph node « . The longer the multiterm concepts, the more detailed becomes their meaning and the more difficult it is to find equal correspondences. Although FMA contains 11 different concepts that encompass the string » paratracheal lymph node « in the preferred name, e.g. » set of paratracheal lymph nodes « , no equal counterpart could be found in FMA.

The inventor used linguistic methods to enhance the number of alignment correspondences. For instance, by applying the trigram mapping function $\pi_{trigram}$, the inventor could enhance the number of mappings by number 6.9 (starting from 64=$|\pi_{eq}|$), and by applying the linguistic fullform and the syntactic variants mapping function it was possible to enhance the number of mappings from 309 to 1,409.

Applying linguistic methods the inventor could continuously improve the recall of the alignment mappings at the cost of the precision measure. The evaluation of the results revealed that about 30% of the established mappings were not correct, since the corresponding concepts contained antonym terms, e.g., » Right buccinator lymph node « and » Left buccinator lymph node « . Therefore, the inventor required some mechanism for filtering incorrect correspondences.

For improving the precision value, the inventor established filtering functions incorporating context information to reflect the particularities of the domain. These filtering functions are used to avoid incorrect alignments.

For instance, the inventor have applied the antonym filtering function $\delta_{ant}$ in combination with the trigram mapping function $\pi_{tri}$ which yields again a mapping function $\delta_{ant} \circ \pi_{tri}$. The evaluation showed that the combination of the two functions helps to significantly improve the precision and F1-Score of the alignment. But one has to keep in mind, that the quality of the result is directly influenced by the declaration of the antonym set $\Omega$.

For each domain, a different set of antonyms has to be expected. The analysis of incorrect mapping results that were produced by the trigram mapping function as well as an antonym thesaurus provided guidance in determining the required antonym pairs. However, in order to cope with the particular meaning of medical terms, clinical evaluation of antonym pairs was required.

According to an embodiment, a connection between an individual set of mapping functions and an individual set of filtering functions is leading to an improved alignment in terms of precision, recall, and F1 measures of the correspondences.

Such a connection may be a combination using a chaining-operand » ○ « and/or a unifying-operand » ∪ « .

For instance, by combining the hypernym filtering function $\delta_{hyp}$ with the antonym filtering function and the trigram, linguistic fullform and syntactic variants mapping function, i.e, $\delta_{hyp} \circ \delta_{ant} \circ (\pi_{tri} \cup \pi_{syn} \cup \pi_{full})$, the inventor could significantly increase the F1-Score from 0.83 to 1.99 with a confidence level of 0.01.

Similar to the definition of the antonym set, the definition of the hypernym set is one of the essential influencing factor for improving the quality of mapping results. The composition of particular mapping functions and filtering functions relies on the domain-specific interpretation and analysis of the evaluation results, the discussion with medical experts, as well as the study of the expressiveness and coverage of the used medical ontology relations.

The various embodiments introduce a formal approach for composing ontology alignments that makes use of linguistic functions, context information and continuous user feedback. The evaluation shows that the incorporation of the context information paves the way for optimized F1 measures. The evaluation shows that axiomatic models in combination with syntactic rules and context information are very effective in their precision, recall, and F1 measures.

FIG. 2 illustrates an exemplary ontology alignment system in accordance with an embodiment. The ontology alignment system 200 includes a source ontology 202 including a plurality of structured information entities, which may be stored in a first memory, and a target ontology 204 including a plurality of structured information entities which may be stored in a second memory. In some embodiments, the first and second memory are a single memory unit.

The ontology alignment system 200 may further include a mapping unit 206 implementing one or more mapping functions. In some embodiments, the mapping functions a an equal mapping function, a trigram mapping function, a linguistic fullform mapping function, and a syntactic variants mapping function. The mapping unit applies the mapping functions to process a set of correspondences between the structured entities of the source ontology and the target ontology.

A restriction unit 210 restricts the set of correspondences by applying one or more filtering functions. In some embodiments, these may include an antonym function and a hypernym function.

An assignment unit 212 assigns an identifier for each mapping function and each filtering function being applied to each of the correspondences.

A composition unit 208 composes a plurality of ontology alignments 201. The ontology alignments are connections between an individual set of mapping functions and an individual set of filtering functions.

An evaluation unit 214 may be used to evaluate an ontology alignment, for example, by rating a relevance of at least one of the plurality of correspondences resulting from the ontology alignment. The relevance may be determined by the degree of relatedness of the information entities being provided by said correspondence.

Embodiments can be implemented in computing hardware (computing apparatus) and/or software, including but not limited to any computer that can store, retrieve, process and/or output data and/or communicate with other computers.

The processes can also be distributed via, for example, downloading over a network such as the Internet. The results produced can be output to a display device, printer, readily accessible memory or another computer on a network. A program/software implementing the embodiments may be recorded on computer-readable media comprising computer-readable recording media.

The program/software implementing the embodiments may also be transmitted over a transmission communication media such as a carrier wave.

Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT).

Examples of the optical disk include a DVD (Digital Versatile Disc), a DVD-RAM, a CD-ROM (Compact Disc—Read Only Memory), and a CD-R (Recordable)/RW.

The invention has been described in detail with particular reference to various embodiments thereof and examples, but it will be understood that variations and modifications can be effected within the spirit and scope of the invention covered by the claims.

What is claimed is:

1. A method of composing an ontology alignment for a plurality of ontologies, executed by one or more processors, comprising:
   providing at least one source ontology from a first memory unit, the source ontology including a plurality of structured information entities;
   providing at least one target ontology from a second memory unit, the target ontology including a plurality of structured information entities;
   processing a set of correspondences between at least one of said structured information entities of said source ontology and at least one of said structured information entities of said target ontology by applying at least one of a plurality of mapping functions;
   at least partially restricting said set of correspondences by applying at least one of a plurality of filtering functions;
   for each of said correspondences assigning an identifier for each mapping function and each filtering function being applied to said correspondence;
   composing a plurality of ontology alignments, each ontology alignment being a connection between an individual set of said plurality of mapping functions and an individual set of said plurality of filtering functions; and
   evaluating an ontology alignment by rating a relevance of at least one of the plurality of correspondences resulting from said ontology alignment, the relevance being determined by the degree of relatedness of the information entities being provided by said correspondence.

2. The method according to claim 1, wherein the plurality of mapping functions comprise at least one of:
   an equal mapping function;
   a trigram mapping function;
   a linguistic fullform mapping function; and
   a syntactic variants mapping function.

3. The method according to claim 1, wherein the plurality of filtering functions include at least one of an antonym function and a hypernym function.

4. The method according to claim 1, wherein at least one of the first memory unit and the second memory unit are formed by one memory unit.

5. A computer program product, which contains a program code stored on a non-transitory computer-readable medium and which, when executed on a computer, carries out a method of composing an ontology alignment for a plurality of ontologies, comprising:
   providing at least one source ontology from a first memory unit, the source ontology including a plurality of structured information entities;
   providing at least one target ontology from a second memory unit, the target ontology including a plurality of structured information entities;
   processing a set of correspondences between at least one of said structured information entities of said source ontology and at least one of said structured information entities of said target ontology by applying at least one of a plurality of mapping functions;
   at least partially restricting said set of correspondences by applying at least one of a plurality of filtering functions;
   for each of said correspondences assigning an identifier for each mapping function and each filtering function being applied to said correspondence;
   composing a plurality of ontology alignments, each ontology alignment being a connection between an individual set of said plurality of mapping functions and an individual set of said plurality of filtering functions; and evaluating an ontology alignment by rating a relevance of at least one of the plurality of correspondences resulting from said ontology alignment, the relevance being determined by the degree of relatedness of the information entities being provided by said correspondence.

6. The computer program product according to claim 5, wherein the plurality of mapping functions comprise at least one of:
an equal mapping function;
a trigram mapping function;
a linguistic fullform mapping function; and
a syntactic variants mapping function.

7. The computer program product according to claim 5, wherein the plurality of filtering functions include at least one of an antonym function and a hypernym function.

8. The computer program product according to claim 5, wherein at least one of the first memory unit and the second memory unit are formed by one memory unit.

9. An apparatus for composing an ontology alignment for a plurality of ontologies, comprising: a processor; comprising:
a first memory unit storing at least one source ontology, the source ontology including a plurality of structured information entities;
a second memory unit for storing at least one target ontology, the target ontology including a plurality of structured information entities;
a mapping unit for processing a set of correspondences between at least one of said structured information entities of said source ontology and at least one of said structured information entities of said target ontology by applying at least one of a plurality of mapping functions;
a restriction unit for restricting said set of correspondences by applying at least one of a plurality of filtering functions;
an assignment unit for assigning an identifier for each mapping function and each filtering function being applied to each of said correspondences;
a composition unit for composing a plurality of ontology alignments, each ontology alignment being a connection between an individual set of said plurality of mapping functions and an individual set of said plurality of filtering functions; and
an evaluation unit for evaluating an ontology alignment by rating a relevance of at least one of the plurality of correspondences resulting from said ontology alignment, the relevance being determined by the degree of relatedness of the information entities being provided by said correspondence.

10. The apparatus according to claim 9, wherein the plurality of mapping functions comprise at least one of:
an equal mapping function;
a trigram mapping function;
a linguistic fullform mapping function; and
a syntactic variants mapping function.

11. The apparatus according to claim 9, wherein the plurality of filtering functions include at least one of an antonym function and a hypernym function.

12. The apparatus according to claim 9, wherein at least one of the first memory unit and the second memory unit are formed by one memory unit.

13. A system of composing an ontology alignment for a plurality of ontologies, comprising:
a processor and a first and second memory unit;
wherein the processor is operable to provide at least one source ontology from the first memory unit, the source ontology including a plurality of structured information entities;
wherein the processor is further operable to provide at least one target ontology from the second memory unit, the target ontology including a plurality of structured information entities;
wherein the processor is further operable to process a set of correspondences between at least one of said structured information entities of said source ontology and at least one of said structured information entities of said target ontology by applying at least one of a plurality of mapping functions;
wherein the processor is further operable to at least partially restrict said set of correspondences by applying at least one of a plurality of filtering functions;
for each of said correspondences, the processor is configured to assign an identifier for each mapping function and each filtering function being applied to provide said correspondence;
wherein the processor is further operable to compose a plurality of ontology alignments, each ontology alignment being a connection between an individual set of said plurality of mapping functions and an individual set of said plurality of filtering functions; and
wherein the processor is further operable to evaluate an ontology alignment by rating a relevance of at least one of the plurality of correspondences resulting from said ontology alignment, the relevance being determined by the degree of relatedness of the information entities being provided by said correspondence.

14. The system according to claim 13, wherein the plurality of mapping functions comprise at least one of:
an equal mapping function;
a trigram mapping function;
a linguistic fullform mapping function; and
a syntactic variants mapping function.

15. The system according to claim 13, wherein the plurality of filtering functions include at least one of an antonym function and a hypernym function.

16. The system according to claim 13, wherein at least one of the first memory unit and the second memory unit are formed by one memory unit.

\* \* \* \* \*